(12) United States Patent
Park et al.

(10) Patent No.: US 11,285,119 B2
(45) Date of Patent: Mar. 29, 2022

(54) ANTI-INFLAMMATORY COMPOSITION

(71) Applicant: NEOPHARM CO., LTD., Daejeon (KR)

(72) Inventors: Ji Yeon Park, Daejeon (KR); Minhee Kim, Bucheon-si (KR); Bu-Mahn Park, Daejeon (KR); Kyung Sook Yoo, Daejeon (KR); Sung Woo Kim, Daejeon (KR); Hye Seong Shin, Ulsan (KR)

(73) Assignee: NEOPHARM CO., LTD., Daejeon (KR)

(*) Notice: Subject to any disclaimer, the term of this patent is extended or adjusted under 35 U.S.C. 154(b) by 0 days.

(21) Appl. No.: 16/342,516

(22) PCT Filed: Aug. 25, 2017

(86) PCT No.: PCT/KR2017/009298
§ 371 (c)(1),
(2) Date: Apr. 16, 2019

(87) PCT Pub. No.: WO2018/074727
PCT Pub. Date: Apr. 26, 2018

(65) Prior Publication Data
US 2019/0262287 A1      Aug. 29, 2019

(30) Foreign Application Priority Data

Oct. 17, 2016 (KR) .................. 10-2016-0134441
Jan. 23, 2017 (KR) .................. 10-2017-0010241

(51) Int. Cl.
| | | |
|---|---|---|
| *A61K 31/16* | (2006.01) | |
| *A61K 8/42* | (2006.01) | |
| *A61K 31/164* | (2006.01) | |
| *A61K 31/198* | (2006.01) | |
| *A61Q 19/00* | (2006.01) | |
| *A61Q 19/08* | (2006.01) | |
| *A61P 17/00* | (2006.01) | |
| *A61K 9/00* | (2006.01) | |

(52) U.S. Cl.
CPC .............. *A61K 31/16* (2013.01); *A61K 8/42* (2013.01); *A61K 9/0014* (2013.01); *A61K 31/164* (2013.01); *A61K 31/198* (2013.01); *A61P 17/00* (2018.01); *A61Q 19/00* (2013.01); *A61Q 19/08* (2013.01)

(58) Field of Classification Search
CPC ..... A23L 33/10; A61K 31/164; A61K 31/195; A61K 31/198; A61K 8/42; A61K 9/0014; A61K 31/16; A61K 9/06; A61P 29/00; A61Q 19/00; A61Q 19/08
USPC ....................................... 514/563
See application file for complete search history.

(56) References Cited

U.S. PATENT DOCUMENTS

| | | | | |
|---|---|---|---|---|
| 6,221,371 B1* | 4/2001 | Baik | ............... | C07C 235/08 |
| | | | | 424/401 |
| 7,879,838 B2* | 2/2011 | Zeng | ............... | C07D 413/14 |
| | | | | 514/210.2 |
| 10,618,874 B2 | 4/2020 | Chung et al. | | |
| 10,695,275 B2 | 6/2020 | Jeong et al. | | |
| 2004/0229817 A1* | 11/2004 | Duggal | ............... | A61K 31/197 |
| | | | | 514/255.03 |
| 2005/0004164 A1* | 1/2005 | Caggiano | ............... | A61P 3/14 |
| | | | | 514/310 |
| 2005/0256132 A1* | 11/2005 | Caggiano | ............... | A61K 31/4406 |
| | | | | 514/254.09 |
| 2006/0094790 A1* | 5/2006 | Park | ............... | A61P 17/00 |
| | | | | 514/625 |
| 2006/0276448 A1* | 12/2006 | Zeng | ............... | A61P 37/00 |
| | | | | 514/210.2 |
| 2007/0299105 A1* | 12/2007 | Caggiano | ............... | A61P 19/10 |
| | | | | 514/310 |
| 2010/0173995 A1* | 7/2010 | Park | ............... | A61K 31/164 |
| | | | | 514/625 |
| 2011/0098229 A1* | 4/2011 | Paul | ............... | A61K 45/06 |
| | | | | 514/18.6 |
| 2014/0309302 A1 | 10/2014 | Koshti et al. | | |

FOREIGN PATENT DOCUMENTS

| | | | | |
|---|---|---|---|---|
| CN | 105979925 A | | 9/2016 | |
| FR | 2855049 A1 * | | 11/2004 | ............. A61K 8/676 |

OTHER PUBLICATIONS

Michael K. Reddy ("Amino acid." Britannica Academic, Encyclopedia Britannica, Dec. 21, 2016. academic.eb.com/levels/collegiate/article/amino-acid/7182).*
Office Action of Chinese Patent Application No. 201780063669. 7—8 pages (dated Dec. 30, 2020), English abstract considered.
International Search Report of corresponding Patent Application No. PCT/KR2017/009299, which is parent—4 pages (dated Nov. 27, 2017).
Albrecht, Martin et al. (DE 10217131, Accession No. 2003:114227 HCAPLUS Document No. 138:142225, 2003.
Smart, Darren et al. (Accession No. 2002: 466981, HCAPLUS Document No. 137:195813, British Journal of Pharmacology (2002), 136(3), 452-458.

(Continued)

*Primary Examiner* — Jared Barsky
(74) *Attorney, Agent, or Firm* — Knobbe, Martens, Olson & Bear, LLP

(57) ABSTRACT

An anti-inflammatory composition is disclosed. The anti-inflammatory composition is be useful for a pharmaceutical composition or a cosmetic composition by not only having excellent stability on the skin and therefore being harmless to the human body, but also by controlling the expression of an inflammatory skin disease-related mediating factor and thereby exhibiting an excellent anti-inflammatory effect.

8 Claims, 2 Drawing Sheets

(56) References Cited

OTHER PUBLICATIONS

International Search Report of corresponding Patent Application No. PCT/KR2017/009298, which is parent—4 pages (dated Nov. 27, 2017).

* cited by examiner

ANTI-INFLAMMATORY COMPOSITION

TECHNICAL FIELD

The present invention relates to an anti-inflammatory composition, and more particularly, to an anti-inflammatory pharmaceutical composition and an anti-inflammatory cosmetic composition having an anti-inflammatory effect by controlling an expression of an inflammatory skin disease-related mediating factor.

BACKGROUND ART

Inflammation is one of the defense reactions of a living body to prevent damage to living tissue due to an increase of blood flow of an infected area, swelling, immune cells and antibody migration, pain, fever, and the like, caused when histamine, kinin, and the like, are released by cell damage caused by external biologic causes (bacteria, viruses, and parasites), physiological causes (mechanical stimulation, heat, radiation, and electricity), chemical causes, and the like, thus resulting in vasodilation, an increase in capillary permeability, and accumulation of macrophages at inflammatory sites.

An inflammatory skin disease generally refers to eczematous dermatitis. The eczema refers to a skin disease in which vesicles (small blisters) with itching, erythema (reddening of the skin), swelling, and the like, are seen in the acute phase, while lichniscation (indicating that lines of skin that are normally present on the skin such as palms become clearer due to dry and firm skin), scale, changes in skin color, and the like, are seen while decreasing the swelling and the vesicle in the chronic phase. Examples of the eczematous dermatitis may include contact dermatitis, atopic dermatitis, and seborrheic dermatitis, and the like.

As described above, the inflammatory response in the skin starts as an action to defend skin damage caused by physical stimulation, chemical substances, bacteria, and the like, and various immune cells and inflammation-inducing cytokines are involved therein. Representative examples of the cytokine may include interleukin, a proliferation factor, chemokine, a tumor necrosis factor, interferon, and the like. Specific examples of the cytokine may include insulin, insulin growth factor (IGF)-I, IGF-II, epidermal growth factor (EGF), transforming growth factor (TGF)-α, TGF-β1, TGF-β2, fibroblast growth factor (FGF)-1, FGF-2, FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, vascular endothelial growth factor (VEGF)-A, VEGF-B, VEGF-C, VEGF-D, nerve growth factor (NGF), interleukin (IL)-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-18, granulocyte macrophage colony stimulating factor (GM-CSF), granulocyte colony stimulating factor (G-CSF), macrophage colony stimulating factor (M-CSF), stem cell factor (SCF), flt-3 ligand (FL), angiopoietin, erythropoietin (EPO), thrombopoietin (TPO), oncostatin M (OSM), leukemia inhibitory factor (LIF), activin, inhibin, bone morphogenetic protein (BMP), platelet-derived growth factor (PDGF), hepatocyte growth factor (HGF), tumor necrosis factor (TNF)-α, TNF-β, Fas ligand (Fas-L), CD40 ligand, macrophage inflammatory protein (MIP), monocyte chemoattractant protein (MCP), interferon (IFN)α, IFNβ, IFNγ, glial cell-derived neurotrophic factor (GDNF), angiotensin, and the like.

Currently, synthetic medicines such as ibuprofen, antihistamines, steroids, cortisone, immunosuppressants, immune promoter, and the like, are used for prevention and treatment of inflammatory skin diseases. However, the treatment effect is temporary, there are many side effects such as simple symptom relief, hypersensitivity reaction, aggravation of the immune system, and the like, and there are limitations on the fundamental treatment of inflammation. In addition, Korean Patent No. 0563548, Korean Patent No. 0697319, Korean Patent No. 1309172 and Korean Patent No. 1141802 disclose various attempts to develop a cosmetic composition having an anti-inflammatory function using a natural extract. However, the use amount of the composition is limited due to another skin irritation, discoloration, or the like, or solubility in water is not good, and thus it is difficult to obtain a substantial effect due to limitation of application when the composition is applied to an actual product.

Thus, the present applicant conducted intensive studies on degree of activity inhibition of inflammation-inducing cytokine which is an inflammatory skin disease-related mediating factor, and as a result, found that a compound derived from specific alcohol or amino acid is not only safe on the skin because the compound has no cytotoxicity, allergenicity, and the like, but also because the compound effectively functions to inhibit production of inflammation-inducing cytokines (particularly, IL-8 and IL-17), and completed the present invention by providing an anti-inflammatory composition including the same.

DISCLOSURE

Technical Problem

An object of the present invention is to provide an anti-inflammatory composition capable of effectively inhibiting skin inflammation and having an excellent skin cell regeneration effect without causing skin side effects.

Technical Solution

In one general aspect, an anti-inflammatory composition includes: a compound represented by Chemical Formula 1 below as an active ingredient:

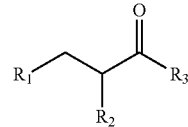

Chemical Formula 1 in Chemical Formula 1, $R_1$ is hydrogen, (C1-C30)alkyl, (C2-C30)alkenyl, (C2-C30)alkynyl, (C1-C30)alkoxy, or hydroxy(C1-C30)alkyl;

$R_2$ is (C1-C30)alkyl, (C2-C30)alkenyl, (C2-C30)alkynyl, (C1-C30)alkoxy, or hydroxy(C1-C30)alkyl; and $R_3$ is

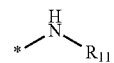

or a substituted or unsubstituted amino acid group, wherein $R_{11}$ is hydroxy(C1-C30)alkyl.

The anti-inflammatory composition according to an embodiment of the present invention may include the above-described compound as an active ingredient to control cytokine and inhibit expression of an inflammation mediating molecule, thereby controlling stimulation and inflammation. In detail, the anti-inflammatory composition according to the present invention has excellent inhibitory effects, particularly, on inflammation-inducing cytokines such as interleukin-8 (IL-8), interleukin-17 (IL-17), and the like.

In other words, the anti-inflammatory composition according to an embodiment of the present invention may increase distribution of a regulatory T cell (Treg) that inhibits an activity of inflammatory cells such as macrophages or neutrophils, thereby effectively inhibiting expression of inflammation to exhibit an excellent anti-inflammatory effect.

The anti-inflammatory composition according to the present invention may be formulated into a pharmaceutical composition or a cosmetic composition including the compound represented by Chemical Formula 1 above as an active ingredient, and the composition has an excellent effect in improving inflammatory skin diseases, particularly, atopic dermatitis and/or allergic dermatitis.

Advantageous Effects

According to the present invention, the regulation of cytokine may be suppressed to effectively prevent the inflammatory reaction, and thus excellent anti-inflammatory effects on inflammatory skin diseases, particularly, atopic dermatitis, allergic dermatitis, and the like, may be exhibited.

Further, the anti-inflammatory composition containing the active ingredient according to the present invention may be safely applied to cosmetic compositions and pharmaceutical compositions of various formulations since the anti-inflammatory composition does not have cytotoxicity and skin side effects.

BEST MODE

Figure 1:
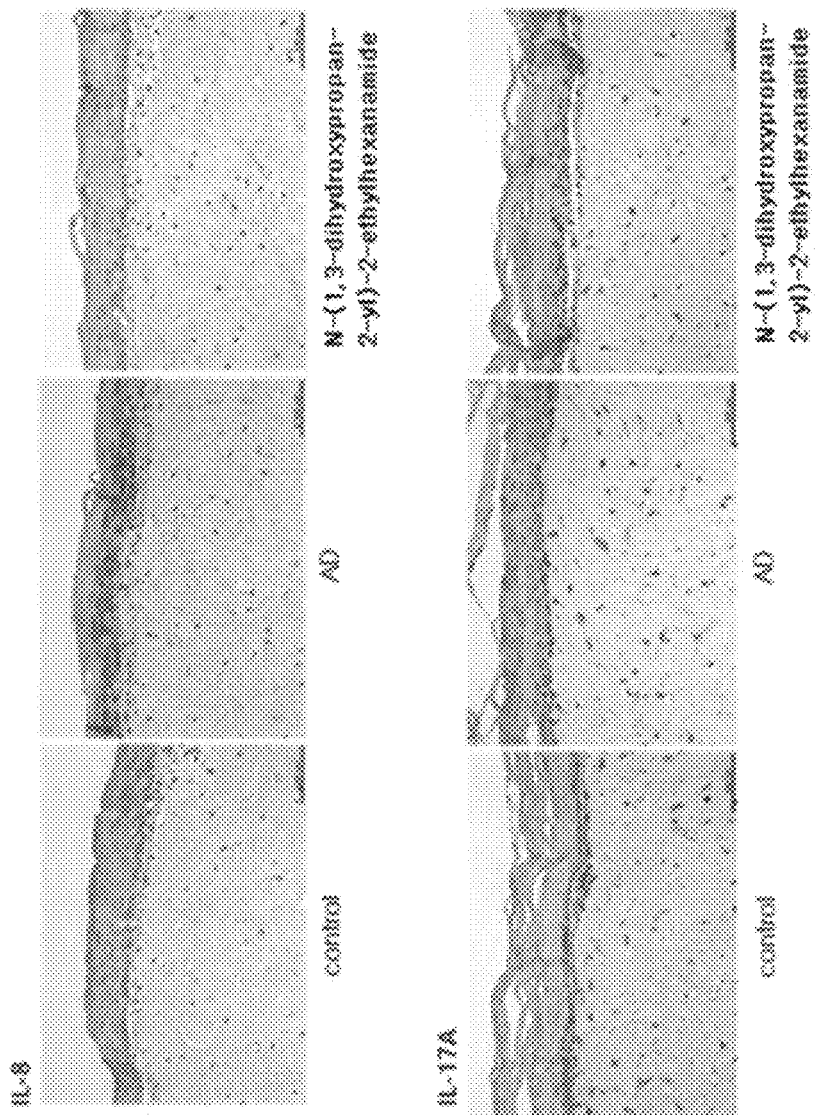
FIG. 1 shows an increase of IL-8 and IL-17A in an atopic dermatitis-induced skin model (AD) as compared with a general skin model, and shows immunohistochemical results in which IL-8 and IL-17A expression was reduced when the anti-inflammatory composition according to the present invention was administered to the atopic dermatitis-induced skin model, similar to that of the general skin model.

Hereinafter, an anti-inflammatory composition according to the present invention is described. Unless otherwise defined, the technical terms and scientific terms used herein have meanings generally understood by those skilled in the art to which the present invention pertains. Known functions and constitutions that may obscure the gist of the present invention with unnecessary detail will be omitted.

The term "inflammation" used herein refers to a phenomenon that is known, for a series of defensive purposes, to minimize a reaction and restore a damaged area to an original state thereof when a cell or tissue is damaged by some cause, and is collectively referred to as causing nerves, blood vessels, and lymph vessels responses, humoral responses, and cellular responses, thus resulting in pain, swelling, redness, fever, and the like, to induce dysfunction. An inflammatory skin disease caused by the inflammation may be at least one selected from the group consisting of atopic dermatitis, psoriasis, contact dermatitis, eczematous dermatitis, actinic dermatitis, seborrheic dermatitis, dermatitis herpetiformis, lichen planus, lichen sclerosus, pyoderma gangrenosum, pemphigus, epidermolysis bullosa, systemic sclerosis, dermatomyositis, polymyositis, inflammatory muscle lesions, leprosy, or Sézary's syndrome, and may include allergic dermatitis such as urticaria, insect allergies, food allergies, and drug allergies, which fall within the same category.

The terms "IL-8" and "IL-17" used herein are one example of an inflammation-inducing cytokine, and an expression thereof is continuously increased by an inflammatory reaction, and thus suppression of the IL-8 and IL-17 is very important to relieve the inflammation. Here, the IL-17 in the present invention may be selected from IL-17A, IL-17B, IL-17C, IL-17D, IL-17E, IL-17F, and the like. Particularly, the anti-inflammatory composition according to the present invention increases distribution of T cells and is superior in inhibiting IL-17A. Thus, for the term "IL-17" used in the present invention, IL-17A is preferred.

The term "application" used herein refers to contacting the composition according to the present invention to the skin of a subject by any suitable method, and has a purpose of absorbing the composition into the skin by the application.

The term "improvement" used herein refers to all actions that improve the inflammatory state or change the inflammatory state beneficially by the application of the composition according to the present invention.

As a result of conducting intensive studies on the degree of activity inhibition of inflammation-inducing cytokine which is an inflammatory skin disease-related mediating factor, the present applicant found that the compound represented by Chemical Formula 1 below effectively inhibited production of interleukin-8 and interleukin-17A which are inflammation-inducing cytokines.

In other words, according to the present invention, it is possible to implement an excellent anti-inflammatory effect by inhibiting production of an inflammatory skin disease-related mediating factor.

[Chemical Formula 1]

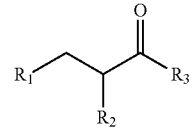

in Chemical Formula 1, $R_1$ is hydrogen, (C1-C30)alkyl, (C2-C30)alkenyl, (C2-C30)alkynyl, (C1-C30)alkoxy, or hydroxy(C1-C30)alkyl;

$R_2$ is (C1-C30)alkyl, (C2-C30)alkenyl, (C2-C30)alkynyl, (C1-C30)alkoxy, or hydroxy(C1-C30)alkyl; and $R_3$ is

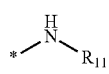

or a substituted or unsubstituted amino acid group, wherein $R_{11}$ is hydroxy(C1-C30)alkyl.

The terms "alkyl", "alkoxy", and other substituents including "alkyl" part used herein may include all linear or branched types. Further, the alkyl, alkoxy, and hydroxyalkyl according to the present invention preferably have 1 to 7 carbon atoms in a linear form or a linear form with 1 to 7 carbon atoms, but an alkyl, alkoxy and hydroxyalkyl having 8 to 30 carbon atoms may also be an embodiment of the present invention.

Further, "alkenyl" used herein is a linear or branched hydrocarbon including one or more double bonds. For example, the alkenyl may be ethenyl, prop-1-en-1-yl, prop-1-en-2-yl, prop-2-en-1-yl, prop-2-en-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, and the like, but is not limited thereto. The term "alkynyl" used herein is a linear or branched hydrocarbon including one or more triple bonds. For example, the alkynyl may be ethynyl, prop-1-yn-1-yl, prop-2-yn-1-yl, but-1-yn-1-yl, but-1-yn-3-yl, but-3-yn-1-yl, and the like, but is not limited thereto.

In addition, the composition according to an embodiment of the present invention may promote skin lipid biosynthesis by containing the compound as an active ingredient. In detail, according to the present invention, the differentiation of skin keratinocytes is promoted to restore skin barrier function and to overcome skin pulling and roughness.

In other words, the composition according to an embodiment of the present invention is preferably an anti-inflammatory composition, and may also be effectively useful as a composition for skin moisturizing, skin keratinocyte differentiation promotion, and/or skin barrier function recovery.

The compound according to an embodiment of the present invention is a very stable material and is easy to formulate. Preferably, $R_1$ may be (C1-C20)alkyl, (C1-C20)alkoxy, or hydroxy(C1-C20)alkyl having a linear form particularly from the viewpoint of exhibiting the anti-inflammatory effect effective for atopic dermatitis, allergic dermatitis, or the like.

Further, in the anti-inflammatory composition according to an embodiment of the present invention, $R_1$ and $R_2$ may be each independently ethyl, n-propyl, n-butyl, or n-pentyl from the viewpoint of having excellent solubility and compatibility with a solvent.

In the anti-inflammatory composition according to an embodiment of the present invention, from the viewpoint of having excellent solubility and compatibility with a solvent, being safe in a living body, and having an anti-inflammatory effect, preferably, $R_3$ of the compound may be selected from the following structures:

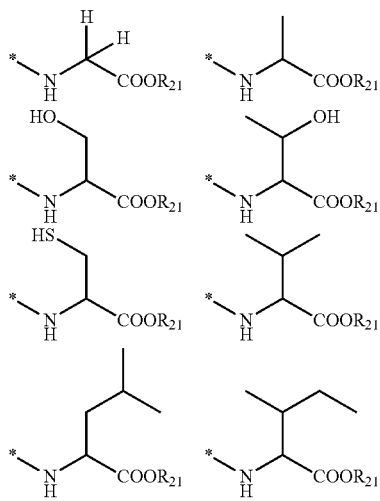

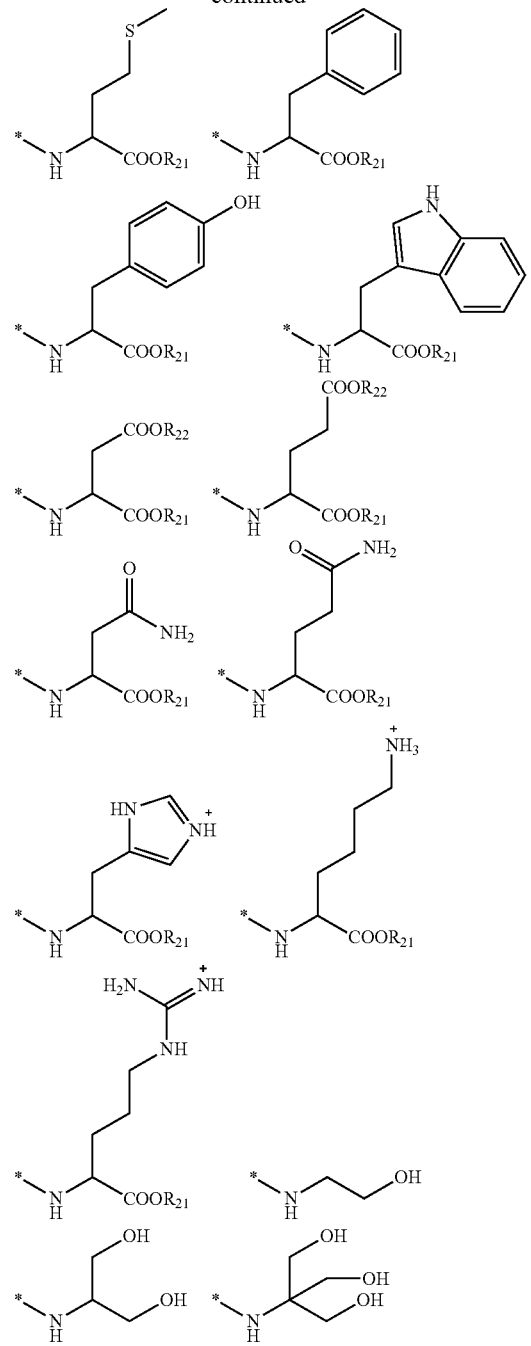

in structures above, $R_{21}$ and $R_{22}$ are each independently hydrogen or (C1-C7) alkyl.

In the anti-inflammatory composition according to an embodiment of the present invention, it is preferable that $R_{21}$ and $R_{22}$ of the compound are each independently selected from methyl, ethyl, and propyl, but are not limited thereto.

The compound according to an embodiment of the present invention is a very stable substance and is easy to formulate. Particularly, from the viewpoint of exhibiting the anti-inflammatory effect effective for atopic dermatitis, allergic dermatitis, or the like, more preferably, $R_3$ of the compound may be a hydroxy(C3-C4)alkyl in a branched form, and as a more preferred example, may be a compound represented by Chemical Formula 2 below, but is not limited thereto.

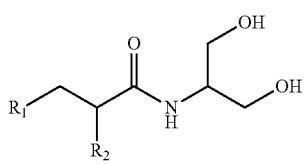

[Chemical Formula 2]

in Chemical Formula 2,
R₁ is hydrogen, (C1-C7)alkyl or hydroxy(C1-C7)alkyl, and
R₂ is (C1-C7)alkyl or hydroxy(C1-C7)alkyl.

Further, the present applicant also found that the anti-inflammatory composition including the compound represented by Chemical Formula 1 as an active ingredient may be formulated into a cosmetic composition, a pharmaceutical composition, and the like. An amount range of the compound may be appropriately adjusted according to requirements such as inhibition of cytokine activity, skin safety, easiness of formulation, and the like. In the cosmetic composition and/or the pharmaceutical composition, the amount range of the active ingredient is not limited, but may be 0.001 to 50 wt %, preferably 0.01 to 30.0 wt %, and more preferably 0.01 to 20.0 wt % based on the total weight of the composition.

Hereinafter, the anti-inflammatory cosmetic composition according to an embodiment of the present invention is described in detail.

The cosmetic composition according to the present invention may be prepared by including suitable additives conventionally used. Here, examples of the additive may include one or more selected from one or more aqueous additives selected from purified water, stabilizers, emulsifiers, thickeners, moisturizers, liquid crystal membrane strengthening agents, pH regulators, antibacterial agents, water-soluble polymers, coating agents, metal ion sequestering agents, amino acids, organic amines, polymer emulsions, pH adjusters, skin nutrients, antioxidants, antioxidant aids, preservatives, flavoring, and the like; and one or more oil additives selected from oils, waxes, hydrocarbon oils, higher fatty acid oils, higher alcohols, synthetic ester oils, silicone oils, and the like.

The aqueous additive according to an embodiment of the present invention is not limited as long as it is a raw material generally used in the art. Specific examples may include glycerin, dipropylene glycol, butyleneglycol, pentylene glycol, methylpropanediol, sorbitol, diglycerin, erythritol, pentaerythritol, polybutylene glycol-10, polyglycerin-3, polyglycerin-4, polyglycerin-6, polyglycerin-10, polyglycerin-20, polyglycerin-40, sorbes-5, sorbes-6, sorbes-20, sorbes-30, sorbes-40, inositol, maltitol, maltose, mannan, mannitol, mannose, lactitol, lactose, dihydroxypropyl PG-glucoside, dithiaoctanediol, fructose, glucamine, methylglucamine, glucose, 1,2,6-hexanethiol, methyl gluceth-10, methyl gluceth-20, ozonized glycerin, phytantriol, thioglycerin, threitol, trimethylolpropane, xylitol, EDTA, guar gum, quince seed, carrageenan, galactan, gum arabic, pectin, mannan, starch, xanthan gum, curdlan, methylcellulose, hydroxyl ethylcellulose, carboxymethyl cellulose, methyl hydroxypropylcellulose, chondroitin sulfate, dermatan sulfate, glycogen, heparan sulfate, hyaluronic acid, sodium hyaluronate, tragacanth gum, keratan sulfate, chondroitin, mucoitin sulfate, hydroxyethyl guar gum, carboxymethyl guar gum, dextran, keratosulfuric acid, locust bean gum, succinoglucan, charonin acid, chitin, chitosan, carboxymethyl chitin, agar, polyvinyl alcohol, polyvinyl pyrrolidone, carboxyvinyl polymer, sodium polyacrylate, polyethylene glycol, bentonite, methyl paraben, propyl paraben, phenoxyethanol, 1,2-hexanediol, ethylhexyl glycerin, and the like. Further, the oil additive is not limited as long as it is a raw material generally used in the art, and may include, for example, liquid oils such as olive oil, camellia oil, jojoba oil, triglyceride, trioctanoic acid glycerin, triisopalmitic acid glycerin, and the like, solid oils such as palm oil, hardened palm oil, palm oil, hardened oil, and hardened castor oil, and the like, beeswax, candelilla wax, carnauba wax, lanolin, jojoba wax, and the like. Examples of the hydrocarbon oil may include liquid paraffin, squalane, petrolatum, microcrystalline wax, and the like. Examples of the higher fatty acid may include waxes such as lauric acid, myristic acid, palmitic acid, stearic acid, behenic acid, and the like, cetyl alcohol, stearyl alcohol, behenyl alcohol, myristyl alcohol, cetostearyl alcohol, and the like. Examples of the synthetic ester oil may include higher alcohols such as isopropyl myristate, cetyl octanoate, octyldodecyl myristate, isopropyl palmitate, hexyl laurate, myristyl myristate, cetyl lactate, isocetyl isostearate, neopentyl glycol dicaprate, ethylhexyl glycerin, cetyl ethyl hexanoate, ethylhexyl palmitate, cetostearyl alcohol, and the like, chain type silicone oils such as dimethylpolysiloxane, methylphenylpolysiloxane, methylhydrogenpolysiloxane, and the like, cyclic silicone oils such as dodecamethylcyclohexasiloxane, octamethylcyclotetrasiloxane, decamethylcyclopentasiloxane, and the like, but the synthetic ester oil is not limited thereto.

The cosmetic composition according to an embodiment of the present invention may be prepared in the form of a general emulsified formulation, a solubilized formulation, and the like, by using a conventionally known preparation method in addition to the preparation method specifically disclosed in the present invention. Here, the cosmetic composition may be appropriately selected according to the purpose. As a specific example, the cosmetic composition may be formulated into a formulation selected from the group consisting of softening toner, astringent toner, nutritional toner, eye cream, nutritional cream, massage cream, cleansing cream, cleansing foam, cleansing water, powder, essence, and a pack, but is not limited thereto.

Hereinafter, the anti-inflammatory pharmaceutical composition according to an embodiment of the present invention is described in detail.

The anti-inflammatory pharmaceutical composition according to an embodiment of the present invention may include a pharmaceutically acceptable carrier according to a method that may be easily performed by a person skilled in the art to which the present invention belongs. The pharmaceutically acceptable carrier to be included in the anti-inflammatory pharmaceutical composition is conventionally used in the preparation, and may be lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, or mineral oil, but is not limited thereto. The anti-aging pharmaceutical composition of the present invention may further include a lubricant, a wetting agent, a sweetener, a flavor, an emulsifier, a suspension, a preservative, or the like, in addition to the above-described components.

The pharmaceutical composition according to an embodiment of the present invention may be prepared by using a conventionally known preparation method in addition to the preparation method specifically disclosed in the present invention, and may be formulated in an appropriate form according to the purpose. Specific examples thereof may include the forms of, but are not limited to, lotion, ointment, gel, cream, a patch, spray, and the like.

The anti-inflammatory composition according to an embodiment of the present invention has an inflammatory skin disease-improving effect. In particular, the effect of improving atopic dermatitis and/or allergic dermatitis is excellent.

Hereinafter, preferred embodiments of the present invention are described to assist in understanding the present invention. However, the following Examples are provided only for the purpose of easier understanding of the present invention, and the Examples below are merely illustrative and not intended to limit the scope of the present invention in any way.

(Evaluation Method)

1. Confirmation of Cytotoxicity

The cell viability for human fibroblast (ATCC 2076) was measured using the anti-inflammatory composition prepared in the following Examples.

The human fibroblast (ATCC 2076) with a concentration of $5 \times 10^4$ cells/ml was inoculated into a 24-well culture plate of Iscove's Modified Dulbecco's Medium (IMDM, GIBCO) containing 10% bovine serum. After 24 hours of inoculation, the medium was replaced with a serum-free medium, and the test sample was added at a concentration of 0.5, 1, 5 or 10 μg/ml and incubated in a 5% $CO_2$ incubator at 37° C. for one day. Then, the supernatant was removed, the cells were washed with 200 μl of 5% phosphate buffered saline (PBS), 1.0 ml of MTT solution was added to each well, and after 4 hours, and the MTT was removed. Next, 1.0 ml of DMSO was added to each well, and incubation was performed overnight at 37° C. The absorbance at 570 nm was measured to determine the cell viability using Equation 1 below, and results thereof are shown in Table 1 below. Here, as a negative control group, a test group in which the active ingredient was not used was adopted.

Cell viability (%)=($A_{570\lambda.value}/B_{570\lambda.value}$)×100  [Equation 1]

A: Absorbance value at 570 nm of Example
B: Absorbance value at 570 nm of negative control group 2. Confirmation of Safety on Human Skin In order to induce skin irritation, 0.1 wt % of sodium lauryl sulfate (SLS) was used as a positive control. Whether or not the anti-inflammatory composition according to the present invention stimulates the skin was measured by preparing formulations in which respective active ingredients prepared in the following Examples were added in amounts of 0.1, 0.05, and 0.01 wt %, and adhering, for a total of 9 times, 24-hour cumulative patches every other day on the upper forearm in 30 healthy adults using the prepared formulations. A finn chamber (Epitest Ltd, Finland) was used for the patch test, and 15 μl of each of the above-prepared external preparations for skin was added dropwise to the chamber, and the patch was applied. A skin reactivity was confirmed by scoring the degree of skin reaction on each skin using the following Equation 2, and results thereof are shown in Table 2 below. Here, a safe composition is judged when the average skin reactivity is less than 3.

Average skin reactivity=[{Σ(reaction index ($a$)×number of subjects showing reaction ($b$))}/(total number of subjects×highest score (4 points))× 100]=number of tests  [Equation 2]

Reaction index: No visible reaction (0), slight erythema (1), strong erythema (2), strong erythema and edema (3), strong erythema, swelling, and vesicle (4)

3. Measurement of Anti-Inflammatory Effect

In order to measure the anti-inflammatory efficacy, atopic dermatitis was induced with respect to IL-8 and IL-17A, which are inflammation-inducing cytokines, and expression amounts thereof were measured.

Figure 2:
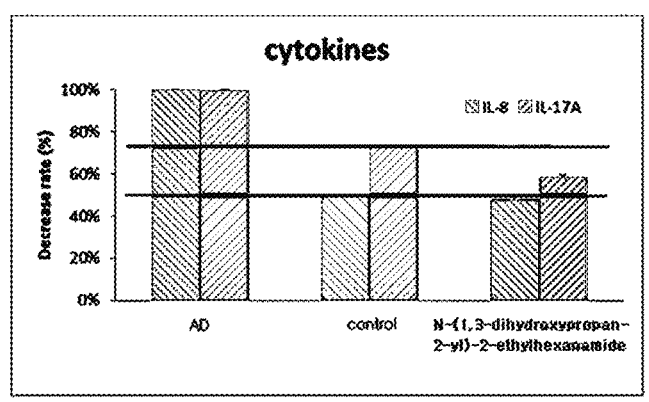
FIG. 2 is a graph showing quantification of the immunohistochemical results obtained in FIG. 1.

In order to induce atopic dermatitis, the 3D culture tissue (EpiDerm Full Thickness 400, sold by MatTek) media containing Poly (I:C), TNF-α, IL-4 and IL-13 were used, and treated for 72 hours with N-(2-hydroxyethyl)octanamide at a final concentration of 100 μM. Then, the 3D culture tissue was immobilized on formalin to make a paraffin block, and the degree of expression of inflammation-inducing cytokine was evaluated. Results thereof are shown in FIGS. 1 and 2.

4. Measurement of Atopic Dermatitis Improvement Effect

In order to measure atopic dermatitis improvement effect, the anti-inflammatory compositions were prepared according to the following Examples. Here, the atopic dermatitis improvement effect was measured using an eczema area severity index (EASI) score. 30 pediatric patients with atopic dermatitis were treated twice a day for 4 weeks, and then effects on atopic symptoms were measured. Here, as a negative control group, a test group in which the active ingredient was not used was adopted.

Example 1

Step 1.

2-Ethylhexanoic acid (1.9 mmol), 1-(3-dimethylaminopropyl)-3-ethylcarbodiimide hydrochloride (2.8 mmol) and 1-hydroxybenzotriazole hydrate (2.8 mmol) were well stirred in dichloromethane (6 ml) and methanol (0.2 ml). Serinol (2.1 mmol) was added, triethylamine (5.7 mmol) was slowly added dropwise, and the mixture was stirred for 5 hours or more. Water was added to the reaction mixture, and the reaction mixture was extracted with dichloromethane. The organic phase was dried over $MgSO_4$ and distilled under reduced pressure. The crude product was purified by silica gel chromatography (dichloromethane:methanol=20: 1) to obtain the final desired compound N-(1,3-dihydroxypropan-2-yl)-2-ethylhexanamide (Yield: 23.5%).

MS (ESI pos, ion) m/z 218 ($MH^+$), 240 (M+Na), C11H23NO3, Exact mass calculated: 217.17

$^1$H-NMR (600 MHz, DMSO): 7.42-7.41 (d, 1H), 4.56-4.54 (m, 2H), 3.77-3.72 (m, 1H), 3.42-3.36 (m, 4H), 2.08-2.04 (m, 1H), 1.46-1.38 (m, 2H), 1.34-1.13 (m, 6H), 0.83 (t, 3H), 0.78 (t, 3H)

Step 2.

An anti-inflammatory composition containing 1.0 wt % (in $H_2O$) of N-(1,3-dihydroxypropan-2-yl)-2-ethylhexanamide prepared in step 1 above was prepared.

The anti-inflammatory composition prepared by the above-described method showed no cytotoxicity in the concentration range of the evaluation method described above (see Table 1). In addition, as a result of confirming safety on human skin, it could be confirmed that the average skin reactivity was 0.93 (when 0.1 wt % of the composition was used), and thus the composition was very safe on the skin (see Table 2).

In FIG. 1, AD represents a skin model in which atopic dermatitis was induced, and the anti-inflammatory effect was evaluated based on the expression amounts of IL-8 and IL-17A.

As a result, it was confirmed that by treating the anti-inflammatory composition according to the present invention with the skin model in which atopic dermatitis was induced, IL-8 and IL-17A expression amounts could be implemented at a similar level to that of normal skin model, which is the control, and thus it was confirmed that the composition of the present invention showed an excellent effect on atopic dermatitis.

Further, the inhibitory effect of each cytokine was quantified based on the results obtained through the immunohistochemistry obtained in FIG. 1, and shown in FIG. 2.

As a result, it was confirmed that the anti-inflammatory composition according to the present invention showed not only IL-8 inhibitory effect by 48.5% or more but also IL-17A inhibitory effect by 58.9% or more as compared with the skin model in which atopic dermatitis was induced.

Further, it was confirmed that as a result of measuring the atopic dermatitis improvement effect, a significant numerical decrease was exhibited.

Example 2

Step 1.

2-Hexyloctanoic acid (0.44 mmol), 1-(3-dimethylaminopropyl)-3-ethylcarbodiimide hydrochloride (0.66 mmol), and 1-hydroxybenzotriazole hydrate (0.66 mmol) were well stirred in dichloromethane. L-tyrosine methyl ester hydrochloride (0.48 mmol) was added, triethylamine (1.3 mmol) was slowly added dropwise, and the mixture was stirred for 5 hours or more. Water was added to the reaction mixture, and the reaction mixture was extracted with dichloromethane. The organic phase was dried over $MgSO_4$ and distilled under reduced pressure. The crude product was purified by silica gel chromatography (dichloromethane:methanol=50:1) to obtain the final desired compound methyl(2-hexyloctanoyl)-L-tyrosinate (Yield: 43.1%).

MS (ESI pos, ion) m/z 406 ($MH^+$), 428 (M+Na), $C_{24}H_{39}NO_4$, Exact mass calculated: 405.29

$^1$H-NMR (600 MHz, $CDCl_3$): 6.99-6.97 (d, 2H), 6.74-6.72 (m, 2H), 5.84-5.82 (d, 1H), 5.23 (s, 1H), 4.93-4.90 (m, 1H), 3.73 (s, 3H), 3.09-2.99 (m, 2H), 2.02-1.97 (m, 1H), 1.55-1.49 (m, 2H), 1.39-1.33 (m, 2H), 1.29-1.11 (m, 16H), 0.89-0.86 (m, 6H)

Step 2.

An anti-inflammatory composition containing 1.0 wt % (in $H_2O$) of methyl (2-hexyloctanoyl)-L-tyrosinate prepared in step 1 above was prepared.

TABLE 1

|  | Used amount (μM) | Cell viability (%) |
|---|---|---|
| Example 1 | 250 | 108% |
|  | 50 | 101% |
|  | 10 | 101% |
|  | 2 | 101% |
|  | 0.4 | 98% |
|  | 0.08 | 100% |
|  | 0.016 | 99% |
|  | 0.0032 | 106% |
|  | 0.00064 | 110% |
| Negative control group | — | 100% |

According to the results shown in Table 1 above, no significant cytotoxic effect was observed when compared with the test group (negative control group) in which the active ingredient was not used even after treatment up to 250 uM concentration.

TABLE 2

|  | Used amount (wt %) | Skin average reactivity |
|---|---|---|
| Example 1 | 0.1 | 0.93 |
|  | 0.05 | 0.46 |
|  | 0.001 | 0.28 |
| Control group | 0.1 | 4.17 |

According to the results shown in Table 2 above, no significant skin irritation was observed even after treatment up to the concentration of 0.1 wt %, and it could be determined that the composition had very excellent stability compared to the positive control group treated with SLS.

Thus, the anti-inflammatory composition according to the present invention is expected to be useful for various types of inflammatory skin diseases since the composition has excellent inhibitory effect on the expression of inflammatory skin disease-related mediating factor.

Although specific embodiments of the present invention are described in detail, it will be apparent to those skilled in the art that the specific description is merely an embodiment and should not be construed as limiting the scope of the present invention. Therefore, the substantial scope of the present invention is defined by the accompanying claims and equivalent thereof.

The invention claimed is:

1. A method of treating an atopic dermatitis in a subject in need of such treatment, the method comprising:
    administering a composition to the subject in an amount effective to inhibit expression of IL-8 or IL-17, wherein the composition comprises a compound represented by Chemical Formula 1:

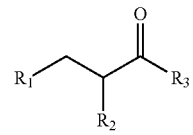

Chemical Formula 1 wherein $R_1$ is hydrogen or C1-C7 alkyl;

wherein $R_2$ is C1-C7 alkyl; and wherein $R_3$ is

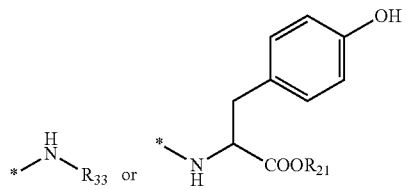

wherein $R_{11}$ is hydroxy C1-C7 alkyl and R21 is hydrogen or C1-C7 alkyl.

2. The method of claim 1, wherein the compound is represented by Chemical Formula 2:

Chemical Formula 2

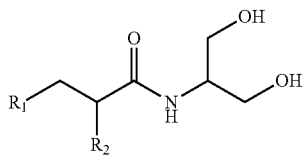

wherein $R_1$ is hydrogen or C1-C7 alkyl.

3. The method of claim 1, wherein the compound has an amount of 0.001 to 50 wt % based on the total weight of the composition.

4. The method of claim 1, wherein administering the composition comprises topically administering the composition onto a skin of the subject.

5. The method of claim 4, wherein the composition is formulated as softening toner, astringent toner, nutrition toner, eye cream, nutrition cream, massage cream, cleansing cream, cleansing foam, cleansing water, powder, essence, or a pack.

6. The method of claim 4, wherein the composition is formulated as lotion, ointment, gel, cream, a patch, or spray.

7. The method of claim 1, wherein $R_3$ is

and $R_{11}$ is hydroxy C1-C7 alkyl.

8. The method of claim 7, wherein $R_{11}$ is hydroxy-C3-alkyl.

* * * * *